(12) United States Patent
Kimball (10) Patent No.: US 7,618,376 B2
(45) Date of Patent: Nov. 17, 2009

(54) DEVICE FOR ASSESSING PERFUSION FAILURE IN A PATIENT BY MEASUREMENT OF BLOOD FLOW

(75) Inventor: Victor E. Kimball, St. Louis Park, MN (US)

(73) Assignee: Vasamed, Inc., Eden Prairie, MN (US)

( * ) Notice: Subject to any disclaimer, the term of this patent is extended or adjusted under 35 U.S.C. 154(b) by 165 days.

(21) Appl. No.: 11/924,862

(22) Filed: Oct. 26, 2007

(65) Prior Publication Data

US 2008/0103378 A1    May 1, 2008

Related U.S. Application Data

(62) Division of application No. 10/668,750, filed on Sep. 23, 2003.

(51) Int. Cl.
*A61B 5/00* (2006.01)
(52) U.S. Cl. .................. 600/485; 600/482; 600/363
(58) Field of Classification Search ........................ None
See application file for complete search history.

(56) References Cited

U.S. PATENT DOCUMENTS

| | | |
|---|---|---|
| 3,511,227 A | 5/1970 | Johnson |
| 3,905,889 A | 9/1975 | Macur et al. |
| 4,016,863 A | 4/1977 | Brantigan |
| 4,109,647 A | 8/1978 | Stern et al. |
| 4,228,805 A | 10/1980 | Rosen et al. |
| 4,324,258 A | 4/1982 | Huebscher et al. |
| 4,381,011 A | 4/1983 | Somers, 3rd |

(Continued)

FOREIGN PATENT DOCUMENTS

WO    WO 94/23645    4/1994

(Continued)

OTHER PUBLICATIONS

Benazzo et al., "Endothelin-Induced Vasoconstriction in Rabbit Nasal Mucosa," *Acta Otolatyngol* (Stockh), vol. 114(5), pp. 544-546 (1994).

(Continued)

*Primary Examiner*—Robert L Nasser
(74) *Attorney, Agent, or Firm*—Barbara A. Wrigley; Oppenheimer Wolff & Donnelly LLP (57) ABSTRACT

A device is provided for assessing impairment of blood circulation in a patient, such as that in perfusion failure, by measurement of blood flow adjacent a mucosal surface accessible by a mouth or nose and connecting with the gastrointestinal tract or upper respiratory/digestive tract of a patient. The device includes a blood-flow sensor adapted to be positioned adjacent a mucosal surface with a patient's body and measuring blood flow in adjacent tissue and a $PCO_2$ sensor adapted to be positioned adjacent the mucosal surface and measuring $PCO_2$. In addition a pH sensor may be used in combination with the blood flow determination. A method of detecting perfusion failure is also disclosed. The method includes utilizing blood-flow measurements in conjunction with a surface perfusion pressure index and/or an optical plethysmography index to more accurately assess perfusion failure. These measurements may also be supplement by taking measurements of pH, sublingual $PCO_2$, and $SaO_2$. The invention affords rapid measurement and detection of perfusion failure.

14 Claims, 4 Drawing Sheets

U.S. PATENT DOCUMENTS

| | | | |
|---|---|---|---|
| 4,503,859 A | 3/1985 | Petty | |
| 4,535,786 A | 8/1985 | Kater | |
| 4,538,618 A | 9/1985 | Rosenberg et al. | |
| 4,577,109 A | 3/1986 | Hirschfeld | |
| 4,590,948 A | 5/1986 | Nilsson | |
| 4,596,254 A | 6/1986 | Adrian et al. | |
| 4,632,119 A | 12/1986 | Reichstein | |
| 4,643,192 A | 2/1987 | Fiddian-Green | |
| 4,729,384 A | 3/1988 | Bazenet | |
| 4,729,824 A | 3/1988 | Gilner | |
| 4,759,374 A | 7/1988 | Kierney et al. | |
| 4,785,814 A | 11/1988 | Kane | |
| 4,789,453 A | 12/1988 | Eberhard et al. | |
| 4,800,886 A | 1/1989 | Nestor | |
| 4,816,131 A | 3/1989 | Bomsztyk | |
| 4,833,091 A | 5/1989 | Leader | |
| 4,834,101 A | 5/1989 | Collison | |
| 4,842,783 A | 6/1989 | Blaylock | |
| 4,890,619 A | 1/1990 | Hatschek | |
| 4,892,383 A | 1/1990 | Klainer et al. | |
| 4,919,891 A | 4/1990 | Yafuso et al. | |
| 4,945,896 A | 8/1990 | Gade | |
| 4,966,148 A | 10/1990 | Millar | |
| 4,981,470 A | 1/1991 | Bombeck, IV | |
| 5,006,314 A | 4/1991 | Gourley et al. | |
| 5,098,659 A | 3/1992 | Yim et al. | |
| 5,105,812 A | 4/1992 | Corman | |
| 5,117,827 A | 6/1992 | Stuebe et al. | |
| 5,158,083 A | 10/1992 | Sacristan et al. | |
| 5,166,990 A | 11/1992 | Riccitelli et al. | |
| 5,174,290 A | 12/1992 | Fiddian-Green | |
| 5,251,619 A | 10/1993 | Lee | |
| 5,280,548 A | 1/1994 | Atwater et al. | |
| 5,329,922 A | 7/1994 | Atlee | |
| 5,330,718 A | 7/1994 | Hui et al. | |
| 5,341,803 A | 8/1994 | Goldberg | |
| 5,368,027 A | 11/1994 | Lubbers et al. | |
| 5,408,999 A | 4/1995 | Singh et al. | |
| 5,411,022 A | 5/1995 | McCue | |
| 5,423,320 A | 6/1995 | Salzman et al. | |
| 5,453,248 A | 9/1995 | Olstein | |
| 5,456,251 A | 10/1995 | Fiddian-Green | |
| 5,479,923 A | 1/1996 | Rantala | |
| 5,536,783 A | 7/1996 | Olstein et al. | |
| 5,579,763 A | 12/1996 | Weil et al. | |
| 5,607,644 A | 3/1997 | Olstein et al. | |
| 5,620,000 A | 4/1997 | Zinser et al. | |
| 5,631,340 A | 5/1997 | Olstein | |
| 5,672,515 A | 9/1997 | Furlong | |
| 5,714,121 A | 2/1998 | Alderete et al. | |
| 5,743,259 A | 4/1998 | Kruse | |
| 5,778,878 A | 7/1998 | Kellam | |
| 5,788,631 A | 8/1998 | Fiddian-Green | |
| 6,055,447 A | 4/2000 | Weil et al. | |

FOREIGN PATENT DOCUMENTS

| | | | |
|---|---|---|---|
| WO | WO 98/20794 | 5/1998 | |

OTHER PUBLICATIONS

Bertuglia et al., "Venular Oscillatory Flow During Hemorrhagic Shock and No Inhibition in Hamster Cheek Pouch Microcirculation," *Microvascular Research*, vol. 54, pp. 23-242 (1997).

Casasco et al., "Occurrence, Distribution and Possible Role of the Regulatory Peptide Endothelin in the Nasal Mucosa," *Cell & Tissue Research*, vol. 274(2), pp. 241-247 (1993).

Friberg et al., "Habitual Snorers and Sleep Apnoics Have Abnormal Vascular Reactions of the Soft Palatal Mucosa on Afferent Nerve Stimulation," *The Laryngoscope*, vol. 108(3), pp. 431-436 (1998).

Grudemo et al., "Rhinostereometry and Laser Doppler Flowmetry in Human Nasal Mucosa: Changes in Congestion and Microcirculation During Intranasal Histamine Challenge," *ORL*, vol. 59, pp. 50-56 (1997).

Grudemo et al., "Studies of Spontaneous Fluctuations in Congestion and Nasal Mucosal Microcirculation and the Effects of Oxymetazoline Using Rhinostereometry and Micromanipulator Guided Laser Doppler Flowmetry," *American Journal of Rhinology*, vol. 13(1), pp. 1-6 (1999).

Hoke et al., "Blood-Flow Mapping of Oral Tissues by Laser Doppler Flowmetry," *International Journal of Oral & Maxillofacial Surgery*, vol. 23(5), pp. 312-315 (1994).

Jin et al., "Decreases in Organ Blood Flows Associated with Increase in Sublingual $PCO_2$ During Hemorrhagic Shock," *J. Applied Physiol.*, vol. 85(6), pp. 2360-2364 (1998).

Kelley et al., "Comparison Between the Uptake of Nitrous Oxide and Nitric Oxide in the Human Nose," *Journal of Applied Physiology*, vol. 85(4), pp. 1203-1209 (1998).

Klinger et al., "Untersuchungen zur Mikro-zirkulation der Nasenschleimhaut bei Verwendung von Ballon-tamponaden," ("The Influence of Cuffed Epistaxis Catheters on Nasal Mucosa Blood Flow Measured by Laser Doppler Flowmety") *Laryngo-Rhino-Otologie*, vol. 76, pp. 127-130 (1997).

Lacroix et al., "Sympathetic Vascular Control of the Pig Nasal Mucosa (III): Co-Release of Noradrenaline and Neuropeptide Y," *Acta Physiologica Scandinavica*, vol. 135(1), pp. 17-28 (1989).

Marais et al., "A Preliminary Comparison of the Effects of Halothane and Isoflurane on Nasal Mucosal Blood Flow," *Rhinology*, vol. 31(1), pp. 31-83 (1993).

Weaver et al., "Effect of Internal Maxillary Arterial Occlusion on Nasal Blood Flow in Swine," *The Laryngoscope*, vol. 109(1), pp. 8-14 (1999).

Ylipaavalniemi et al., "Effect of Local Anaesthesia on the Blood Perfusion of Oral Mucosa Measured by the Laser Doppler Method," *Proceedings of the Finnish Dental Society*, vol. 79(2), pp. 58-61 (1983).

Jin et al. (1997), "End-Tidal $PCO_2$ Serves as an Indicator of Cardiac Output During Experimental Septic Shock," *Crit. Care Med.* 25(1):A122 (Abstract).

Nakagawa et al. (1997), "Sublingual Capnometry for Quantitation of the Severity of Hemorrhagic Shock," *Shock* 7:14 (Abstract).

Nakagawa et al. (1997), "$ETCO_2$ as Non-Invasive Indicator of Cardiac Output During Hemorrhagic Shock," *Crit. Care Med.* 25(1):A132 (Abstract).

Nakagawa et al. (1997) et al. (1997), "Sublingual Capnography as an Indicator of Perfusion Failure in Human Patients," *Chest* 112:4S (Abstract).

Nakagawa et al. (1998), "Comparison of Sublingual Capnometry with Gastric Capnometry and Lactate as Indicators of the Severity of Hemorrhagic Shock," *Crit. Care. Med.* 26(1):A44 (Abstract).

Ogino et al. (1994), "Reflectance Pulse Oximeter Measuring Central SaO2 From Mouth," Proceedings of the Annual International Conference of the IEEE Engineering in Medicine and Biology Society, Baltimore, 2(16):914-915.

Peterson et al. (1984), "Fiber Optic Sensors for Biomedical Applications," *Science* 224(4645):123-127.

Sato et al. (1997), "Espohageal and Gastric $PCO_2$ Both Serve as Quantitative Indicators of Organ Blood Flow During Hemorrhagic Shock," *Crit. Care Med.* 25(1):A37 (Abstract).

Sato et al. (1997), "Esophageal $PCO_2$ as a Monitor of Perfusion Failure During Hemorrhagic Shock," *Appl. Physiol.* 82(2):558-562.

Seitz (1984), "Chemical Sensors Based on Fiber Optics," *Anal. Chem.* 56(1):16A-34A.

Tang et al. (1988), "Myocardial Preservation During Cardiopulmonary Resuscitation," *Curr. Opin. Crit. Care* 4:155-160.

Vurek et al. (1983), "A Fiber Optic $PCO_2$ Sensor," *Annals Biomed. Engineer* 11:499-510.

Weil (1998), "The Assault on the Swan-Ganz Catheter," *Chest* 113:1379-1386 (1998) (Invited Publication).

Xie et al. (1997) "Sublingual Capnometry for Quantitation of the Severity of Septic Shock," *Shock* 7:13-14 (Abstract).

US 5,596,688, 01/1997, Markle et al. (withdrawn)

DEVICE FOR ASSESSING PERFUSION FAILURE IN A PATIENT BY MEASUREMENT OF BLOOD FLOW

CROSS REFERENCE TO RELATED APPLICATIONS

This application is a divisional of U.S. Ser. No. 10/668,750 filed Sep. 23, 2003.

TECHNICAL FIELD

The present invention relates generally to methods and devices for assessing perfusion failure in a patient.

BACKGROUND OF THE INVENTION

Very low blood flow, or low "systemic perfusion," is typically due to low aortic pressure and can be caused by a number of factors, including hemorrhage, sepsis and cardiac arrest. The body responds to such stress by reducing blood flow to the gastrointestinal tract to spare blood for other, more critical organs. Thus, when there is a reduced flow of blood from the heart, the body directs a higher portion of blood to critical organs, such as the brain, which will not survive long without a continuous supply of blood, while restricting the flow to less critical organs, whose survival is not as threatened by a temporary large reduction in blood flow. For example, blood flow to the splanchnic vasculature which supplies the stomach and intestines, and also the esophagus and oral/nasal cavity, is drastically reduced when there is a reduced blood flow from the heart. For this reason, decreased blood flow to the splanchnic blood vessels is thus an indication of perfusion failure in a patient. Physicians commonly take advantage of this phenomenon by taking $CO_2$ and pH measurements in the stomach and intestine to assess perfusion failure.

Assessment of $CO_2$ concentration in the less critical organs, i.e., those organs to which blood flow is reduced during perfusion failure, has been useful in perfusion assessment. Carbon dioxide production, which is associated with metabolism, continues in tissues even during conditions of low blood flow. The concentration of $CO_2$ builds-up in tissues experiencing low blood flow because $CO_2$ is not rapidly carried away. This $CO_2$ build-up (an increase in partial pressure of $CO_2$ ($PCO_2$)) in the less critical organs in turn results in a decrease in pH in nearby tissue. Therefore, perfusion failure is commonly assessed by measuring pH or $PCO_2$ at these sites, especially in the stomach and intestines. For examples of catheters used to assess pH or $PCO_2$ in the stomach or intestines, see, e.g., U.S. Pat. Nos. 3,905,889; 4,016,863; 4,632,119; 4,643,192; 4,981,470; 5,105,812; 5,117,827; 5,174,290; 5,341,803; 5,411,022; 5,423,320; 5,456,251; and 5,788,631.

The inventors have found that increases in $PCO_2$ may be measured throughout the body, including in accessible organs and tissues fed by splanchnic vessels, and used to assess perfusion failure. For example, the inventors have found that a useful measurement of perfusion failure can be obtained by measuring $CO_2$ in the upper respiratory/digestive tract. In U.S. Pat. No. 5,579,763, a method is described that can be used to accurately assess perfusion failure by measuring $PCO_2$ in the patient's esophagus, rather than in the less accessible stomach and/or intestine as previously practiced in the art. Tests showed that measurements of $PCO_2$ in the esophagus are closely correlated with aortic pressure, and, furthermore, that measurements made in the esophagus are even more closely correlated to aortic pressure than measurements of $CO_2$ in the stomach. More recently, in co-pending, commonly assigned U.S. Pat. No. 6,216,024, the inventors further showed that $PCO_2$ measurements in a patient's mucosal tissues (e.g., mouth, nasal mucosa, and throat) are also closely correlated to aortic pressure. As disclosed in U.S. Pat. No. 6,216,024, the $CO_2$ sensor may be placed at a site within the oral-nasal cavity (e.g., under the tongue at a site in contact with the tongue or the floor of the mouth) where it effectively measures $CO_2$ in the tissue. Since carbon dioxide can readily pass through mucosal surfaces, $CO_2$ generated by metabolic activity occurring in tissue below the mucosal surface that is not carried away by blood flow readily migrates through the mucosal surface, where its build-up provides a good measure of perfusion failure. Placement of a $CO_2$ sensor adjacent a mucosal surface of the upper respiratory/digestive tract thus provides a very good quantification of perfusion failure at all times, including the most critical minutes after the onset of perfusion failure when treatment is likely to be most effective. Thus, mucosal measurements of tissue perfusion can be used to assess perfusion failure in patients.

However, $PCO_2$ and pH are indirect measures of blood flow in tissue, being based upon the build-up of metabolites that result from poor perfusion. In addition, measurements of pH may be complicated by the presence of saliva, food, or stomach acids. $CO_2$ measurements may be affected by ambient $CO_2$, and, since they depend on equilibration with tissue $CO_2$ levels, are slow. Thus, there is a need for a more effective method of assessing perfusion failure that will overcome the problems associated with using $PCO_2$ and pH measurements alone and which will and monitor the effectiveness of methods taken to increase perfusion, e.g., blood infusion or the like.

BRIEF SUMMARY OF THE INVENTION

Methods and devices are provided for assessing impairment of circulatory function in a patient, such as that in perfusion failure, which is indicative of shock, by measurement of blood flow adjacent a mucosal surface accessible via the mouth or nose that connects with the GI tract and/or upper respiratory/digestive tract of a patient. The perfusion of a tissue is a function of both the velocity of blood cells flowing through tissue, and of the number of blood cells, so that the blood flow through tissue is a more direct measurement of tissue perfusion than pH or $CO_2$ measurements used alone. Previously, the belief in the art was that decreased blood flow was a localized phenomenon during perfusion failure. It has now been discovered that decreased blood flow, decreased pH and increases in tissue $CO_2$ occur throughout the body during perfusion failure, and in particular occur not only in the stomach, jejunum, colon and rectum, but also in the esophagus, throat, mouth, nose and associated areas. Thus, new and useful methods and devices are now provided, for assessing perfusion failure and perfusion levels in a patient by measuring blood flow in tissues of the GI tract and/or of the upper respiratory/digestive tract of a patient.

The measurement of blood flow using a sensor to detect perfusion failure can also be used in conjunction with the SPP Index, or the ratio of the measurement of surface perfusion pressure to blood pressure measured at the brachial, toe, thigh or other bodily location or measured by the use of an arterial line placed in the patient's artery. A similar index, the optical plethysmography index, may be used in conjunction with blood flow to obtain a more accurate indication of perfusion failure. The optical plethysmography index is the ratio of the optical plethysmography measurement to blood pressure measured at the brachial, toe, thigh or other bodily location or measured by the use of an arterial line placed in the patient's artery. In a healthy patient, this index would be close to one. Therefore, a decreasing index, i.e. less than one, in either case, would be indicative of perfusion failure or shock.

Further the measurement of blood flow using the sensor in accordance with the present invention can also be used in conjunction with blood pressure measured at the brachial, toe, thigh or other bodily location or measured by the use of an arterial line placed in the patient's artery to obtain a more accurate indication of perfusion failure. Moreover, any of the foregoing indices and measurements can be used alone or in combination with measurements of pH, sublingual $CO_2$ and/or saturated $O_2$ to obtain more accurate indications of perfusion failure.

Thus, new and useful methods and devices are provided for assessing perfusion failure and perfusion levels in a patient by (i) measuring blood flow in tissues of the GI tract and/or of the upper respiratory/digestive tract of a patient; (ii) measuring the SPP and/or optical plethysmography indices; (iii) measuring blood flow in tissues of the GI tract and/or upper respiratory/digestive tract of a patient in accordance with the sensor of the present invention in combination with the SPP and/or optical plethysmography indices; (iv) measuring any combination of the foregoing in combination with the measurements pH, sublingual $CO_2$ and/or saturated $O_2$.

In one embodiment, then, a method is provided for assessing impairment of circulatory function, such as that in perfusion failure in a patient. The method comprises introducing a blood-flow sensor adjacent a mucosal surface that is accessible via the mouth or nose and connects with the GI tract or the upper respiratory/digestive tract of a patient, measuring blood flow in the tissue adjacent the sensor, and providing that measurement for assessment of perfusion failure. Specifically, a blood-flow sensor is placed adjacent a mucosal surface within a patient's body, preferably without passing the sensor down through or beyond the patient's epiglottis, most preferably within the oral or a nasal cavity of the patient. The blood-flow sensor may be introduced sublingually to one side of the frenulum. The invasiveness of such a technique is minimal, being substantially no more than in the use of an oral thermometer. Alternatively, the blood flow sensor may be introduced and placed adjacent any mucosal surface accessible via the mouth or nose including connections to the upper respiratory/digestive tract or the gastrointestinal tract. Preferably, the sensor is a laser-Doppler sensor. The output of the sensor can be detected by a device which electronically converts the sensor output to provide the blood flow in a form that is easily understood by persons viewing the display. The device can optionally further sense the rate of change of blood flow with time to indicate the patient's condition.

Accordingly, in another embodiment the invention features a device for assessing perfusion failure in a patient, where the device is composed of a laser-Doppler blood-flow sensor means for measuring blood flow in a tissue, the sensor means being adapted for lying adjacent a mucosal surface in a patient's body, e.g. in the upper respiratory/digestive tract of a patient, and measuring blood flow in vessels in the mucosal tissue; and an indicating means connected to the sensor means, wherein the indicating means indicates a degree of perfusion failure of the patient associated with the detected blood flow. The device may also include a positioning means for positioning the sensor means adjacent the mucosal surface. In one embodiment, the "positioning means" is a holder designed to fit within the mouth of the patient and hold the sensor in place adjacent the mucosal surface. For example, the holder may be designed to position the sensor adjacent the tongue of a patient, or to position the sensor between the inside of a lip and gum of the patient. Alternatively, the positioning means may be a holder designed to fit within a nares of the patient and hold the sensor in place adjacent the mucosal surface. Alternatively, the positioning means may be adapted to position the sensor adjacent any mucosal surface that connects to the upper respiratory/digestive tract or the gastrointestinal tract, which is accessible via the mouth or nose.

In a further embodiment the invention features a device for use with a blood-flow sensor assembly for assessing perfusion failure of a patient. The device is composed of a sensor holder with a sublingual holder inner portion shaped to fit in the mouth of a patient under the patient's tongue, said holder forming at least one holder passage optionally extending from said holder outer portion to said sublingual holder portion.

In a further embodiment the invention comprises measuring blood flow with a blood-flow sensor and additionally making an indirect measurement of blood flow by making, e.g., a $CO_2$ measurement or a pH measurement, or by making all three such kinds of measurements.

In a further embodiment, the invention comprises measuring blood flow with a blood-flow sensor and additionally measuring either surface perfusion pressure with a perfusion pressure monitoring system and brachial, toe, thigh or arterial pressure to calculate the SPP index; or measuring optical plethysmography with a photoplethysmograph and brachial, toe, thigh or arterial pressure to calculate the optical plethysmography index, to more accurately assess perfusion failure. This measurement may also be used in conjunction with indirect measurements of blood flow including measurements of pH, sublingual $CO_2$ and/or saturated $O_2$.

In a further embodiment, the invention comprises measuring blood flow with a blood-flow sensor and additionally measuring surface perfusion pressure with a perfusion pressure monitoring system and brachial, toe, thigh or arterial pressure to calculate the SPP index; and measuring optical plethysmography with a photoplethysmograph and brachial, toe, thigh or arterial pressure to calculate the optical plethysmography index; and utilizing the combination of the foregoing to more accurately assess perfusion failure. This measurement may also be used in conjunction with indirect measurements of blood flow including measurements of pH, sublingual $CO_2$ and/or saturated $O_2$.

One advantage of the invention is that perfusion can be rapidly assessed in a patient, with measurements being made in just a few seconds.

Another advantage of the invention is that perfusion can be assessed in a patient in a minimally invasive manner, and with minimal discomfort or risk of harm to the patient.

Another advantage of the invention is that perfusion can be assessed in a patient without interference in the measurement by ambient levels of $CO_2$ and without substantial drift of the measurement when used in a continuous monitoring application.

Another advantage of the invention is that perfusion can be assessed in a patient without interference with the measurement by the pH of fluids or food near the sensor.

Another advantage of the invention is that perfusion can be readily assessed in a patient suffering from perfusion failure associated with any of a variety of causes, including, but not limited to physical trauma, infection, hypothermia, cardiogenic shock (e.g., acute myocardial infarction, aneurysm, or arrhythmia), obstructive shock (e.g., pulmonary embolism), hypovolemic shock (e.g., due to hemorrhage or fluid depletion), and distributive shock (e.g., due to sepsis, exposure to toxins, or anaphylaxis). The sensitivity of the methods and devices of the invention further allow for assessment of perfusion across a wide range of perfusion failure severity, thereby providing a means to accurately monitor the patient's condition.

Still another advantage of the invention is that the devices and methods can be readily adapted for use in alert, semiconscious, or unconscious patients, and can be further adapted for accurate assessment of perfusion in a patient for a period lasting for only seconds to minutes to hours or days.

Still another advantage of the invention is that the device and methods of the present invention when used in combination with each other can be used to more accurately detect perfusion failure and shock and/or the onset of perfusion failure and shock.

The novel features of the invention are set forth with particularity in the appended claims. The invention will be best understood from the following description when read in conjunction with the accompanying drawings.

DETAILED DESCRIPTION OF THE INVENTION

Definitions and Nomenclature

Before the present devices, apparatus and methods are disclosed and described, it is to be understood that this invention is not limited to sensor designs, measurement techniques, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise.

We define the term "perfusion failure" as used herein to mean a reduction in blood flow associated with maldistribution of blood through the circulatory system and a reduction in blood flow to a less critical tissue(s) and/or organ(s) relative to blood flow in vital (critical) tissues and organs (e.g., the brain and heart). In general, "perfusion failure" is meant to encompass reduction in blood flow associated with a decrease in blood flow significantly or substantially below that associated with normal perfusion and is an indication of shock.

We define the term "measurement" as used herein to refer to a single measurement or a series of measurements made over time, and which may be taken continuously or intermittently (e.g., at selected time intervals).

We define the term "mucosal surface" as used herein to refer to a surface of a mucous membrane containing or associated with mucus secreting glands, and which lines body passages, tubular structures, and organs, consisting of epithelium, lamina, propria, and, in the digestive tract, a layer of smooth muscle and encompasses, for example, the nasal passages (including the nasal cavity, the middle nasal conchae, the inferior nasal conchae, the choana, the naso-pharyngeal opening of the auditory tube and the auditory tube), the oral cavity (including the mouth and spaces within the mouth such as the sublingual area, the hard palate, the soft palate, and the gingival surfaces), the pharynx, the oropharyngeal passage, the esophagus, the stomach, the jejunum, the colon, and the rectum.

We define the terms "gastrointestinal tract" and "GI tract" as used herein to encompass the entire tract from esophagus to rectum, including, e.g., the esophagus, the stomach, the jejunum, the colon, and the rectum.

We define the term "upper respiratory/digestive tract" as used herein to mean the region of the upper respiratory tract and digestive tract above the stomach. We define the "upper respiratory/digestive tract" to encompass the nasal passages (including the nares (or vestibule of the nasal cavity), the nasal cavity, middle nasal conchae, inferior nasal conchae, choana, the naso-pharyngeal opening of the auditory tube, and the auditory tube), the oral cavity (commonly called the mouth and including the spaces within the mouth such as the floor (e.g., sublingual area) and roof of the mouth (e.g., hard palate), the soft palate, the regions between the lips and gums, and the cheeks and gums), the pharynx (including the nasopharynx, oropharynx and laryngopharynx) and oropharyngeal passage (collectively, commonly called the throat) and the esophagus.

We define the term "auditory tube" (Eustachian tube) as used herein to mean the channel through which the tympanic cavity (middle ear) communicates with the nasopharynx.

We define the term "nasopharynx" as used herein to mean the part of the pharynx that lies above the soft palate; anteriorly it opens into the nasal cavity; inferiorly, it communicates with the oropharynx via the pharyngeal isthmus; laterally it communicates with tympanic cavities via auditory tubes.

We define the term "oral-nasal cavity" as used herein to mean the region of the upper respiratory/digestive tract encompassing the nasal passages (including the nares (or vestibule of the nasal cavity), the nasal cavity, the middle nasal conchae, the inferior nasal conchae, the choana and the pharyngeal opening of the auditory tube), the oral cavity (including the mouth and spaces within the mouth such as the floor (e.g., sublingual area) and roof of the mouth (e.g., hard palate), the soft palate, the regions between the lips and gums, and the inner cheeks and gums), and the pharynx (including the nasopharynx, oropharynx and laryngopharynx) and oropharyngeal passage (collectively, commonly called the throat) extending to the top surface of and in the region of the epiglottis.

We define the term "sublingual" as used herein to refer to a region below or beneath the tongue.

We define the term "adjacent" as used herein (e.g., "adjacent the mucosal surface") to mean near or against, e.g., at a distance from the mucosal surface that allows acceptably accurate measurement of blood flow by blood-flow sensor.

We define the term "patient" as used herein to mean a mammalian subject, preferably a human subject, that has, is suspected of having, or is or may be susceptible to a condition associated with low blood flow, and thus perfusion failure.

We define the term "SPP index" to mean the ratio of the surface perfusion pressure measurement to brachial, toe, thigh or arterial pressure, or any other location on the body where blood pressure may be taken.

We define the term "optical plethysmography index" to mean the ratio of optical plethysmography (the measurement taken by a photoplethysmograph) to brachial, toe, thigh or arterial pressure, or any other location on the body where blood pressure may be taken.

Figure 1:
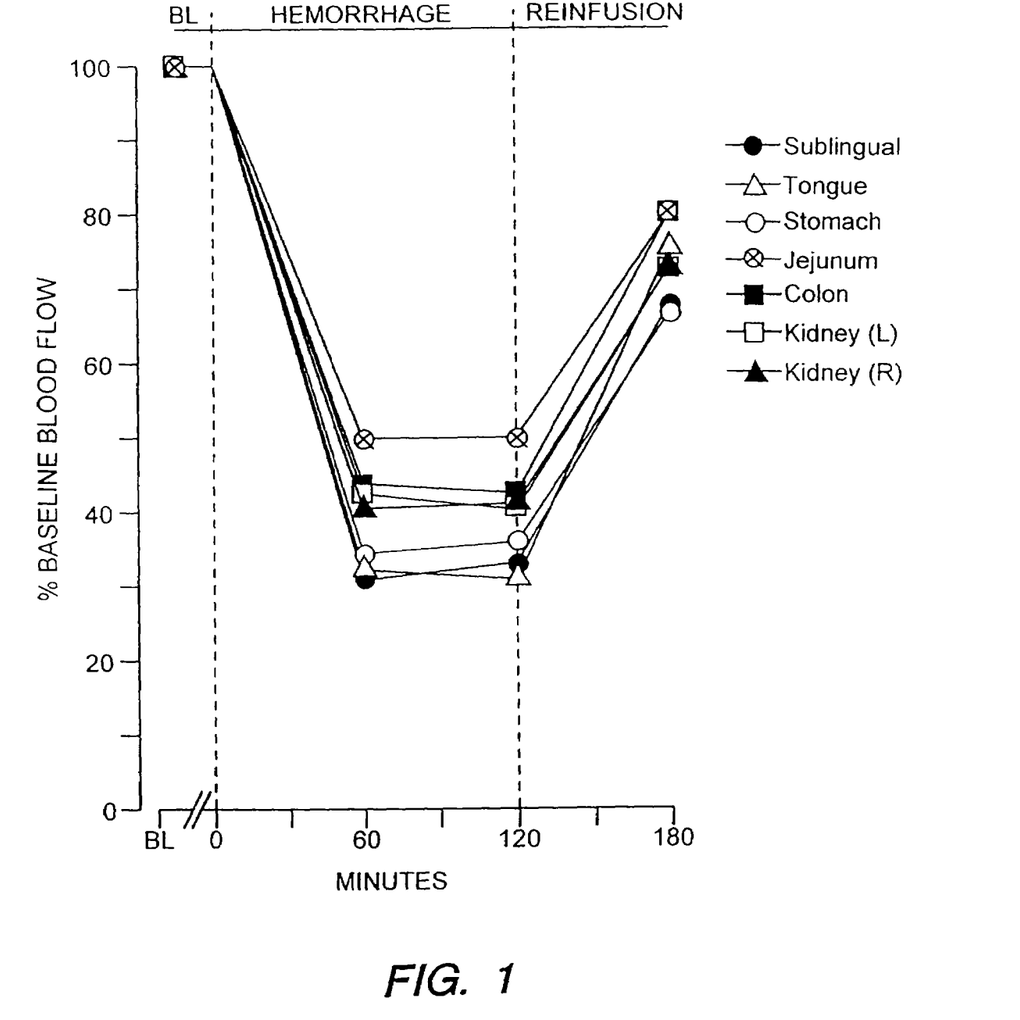
FIG. 1 is a graph showing variation in blood flow in various tissues with time, during an experiment on rats where blood was withdrawn to simulate hemorrhage and so induce perfusion failure, and during reinfusion of blood to allow recovery.

The present invention is based on the inventors' discovery that blood flow decreases throughout the body during perfusion failure, rather than as only a localized phenomenon as previously believed in the art. Evidence for this is seen, e.g., in that tissue $CO_2$ increases in esophagus and sublingual tissue during perfusion failure, as disclosed by the inventors in U.S. Pat. No. 6,216,024. Further evidence of this is shown in FIG. 1 where blood flow in various tissues of experimental animals was measured by the deposition of small beads measured at autopsy. The methods and devices of the invention measure blood flow in tissue at a convenient site within the GI tract or within the upper respiratory/digestive tract, and are thus performed in a minimally invasive manner. In general, these measurements are made by placing a blood-flow sensor such as a laser-Doppler sensor or an ultrasound Doppler sensor adjacent a mucosal surface at a selected site within the upper respiratory/digestive tract and using the sensor to measure blood flow at the selected site. Such measurements may also be made using imaging techniques such as MRI, optical imaging, angiography techniques and other methods as would be known to those skilled in the art.

As blood flows through tissue, the blood cells and the fluid blood plasma move at similar rates. Light, as may be provided by a laser-Doppler blood-flow device, and ultrasound, as may be provided by an ultrasound-Doppler blood-flow device, can pass through tissue to illuminate or impinge upon blood cells moving through tissue of interest. When light or ultrasound reflects off moving blood cells its frequency is shifted in a velocity-dependent manner, a phenomenon known as the "Doppler shift." This phenomenon can be used to measure the velocity of blood cells flowing through the tissue so illuminated or so subject to ultrasound. In addition, a laser-Doppler device or ultrasound-Doppler device may be used to measure the ratio of moving blood cells to the non-moving cells located in the measurement volume of the sensor. The measurement volume of tissue in which this measurement is made may be calculated using scattering theory and the geometry of the illuminating and collecting sites, or may be measured using standard calibration techniques; either of which is routinely done with laser-Doppler devices. The total blood flow may be calculated from these three parameters: 1) the number of cells within the measurement volume, 2) the velocity of the moving cells, and 3) the measurement volume.

Methods and techniques for using laser-Doppler techniques and devices to measure blood flow are known in the art, and may be found in such references as, e.g., U.S. Pat. No. 3,511,227 to Johnson, U.S. Pat. No. 4,596,254 to Adrian et al., and U.S. Pat. No. 4,590,948 to Nilsson.

Methods and techniques for using ultrasound-Doppler techniques and devices to measure blood flow are known in the art, and may be found in such references as U.S. Pat. No. 4,324,258 to Huebscher et al. and U.S. Pat. No. 4,759,374 to Kierney et al. One non-limiting example of a laser-Doppler measurement of surface perfusion pressure is disclosed in U.S. Pat. No. 6,178,342 to Borgos. Borgos discloses a perfusion pressure monitor that measures the "amount" of moving blood contained within a microvascular observation volume in percent tissue hematocrit. The percent hematocrit measurement is taken as a function of applied pressure. An optical probe defines an observation volume in the skin near the surface of the patient. A pressure cuff is used to apply pressure to the patient near the optical probe. The skin perfusion pressure measurement involves the measurement of the pressure within the cuff at the moment that blood within the observation volume is either stationary or expressed from the observation volume. The pressure corresponding to the change in effective percent hemotocrit is the surface perfusion pressure. The instrument used to measure surface perfusion pressure is a monitoring system that includes an optical probe located inside of a pressure cuff. The operator squeezes an inflation bulb to inflate the pressure cuff, or as those skilled in the art will appreciate such a system for inflating may be automated. When the pressure cuff inflates, it positions the optical probe against the skin of the patient's limb. A display instrument, which is coupled to the optical prove via a fiber optic cable, and to the inflation bulb displays the measurement of the number of red blood cells detected within the control volume expressed as a percent hematocrit.

The inventors of the present invention have discovered that the measurement of surface perfusion pressure can be further refined by taking a reference measurement of blood pressure. Blood pressure can be measured at the brachial position, toe, and thigh or may be measured directly via an arterial line inserted in any accessible artery. Blood pressure may also be taken at any other bodily location where blood pressure is commonly measured. The measurement for surface perfusion pressure is then divided by the blood pressure measurement to calculate a resulting index, which the inventor have coined the SPP index. In a healthy patient the SPP index approximates one. Therefore, a decreasing SPP index, i.e. less than one, is indicative of perfusion failure or shock and/or the onset of perfusion failure or shock depending on when the measurement is taken.

A photoplethysmograph for measuring optical plethysmography, on the other hand, uses light absorbance technology to reproduce waveforms produced by pulsating blood. Typically non-visible infrared light is emitted into the skin. More or less light is absorbed, depending on the blood volume in the skin. The backscattered light corresponds with the variation in blood volume. Blood volume changes are then determined by measuring the reflected light and using the optical properties of tissue and blood. The optical plethysmography measurement may be obtained by volume displacement plethysmography or by electrical impedance plethysmography as those skilled in the art can appreciate. Typically the tissue under investigation is bathed with light of a suitable wavelength and the resultant scattered light is measured with a silicon photodiode. The received signal is assumed to be a measure of volume changes due to localized blood flow. Optical plethysmography measurements may be used in conjunction with the blood flow sensor and corresponding measurements in accordance with the present invention. The inventors of the present invention have discovered that optical plethysmography measurements can be further refined by taking a reference measurement of blood pressure. Blood pressure can be measured at the brachial position, toe, and thigh or may be measured directly via an arterial line inserted in any accessible artery. Blood pressure may also be taken at any other bodily location where blood pressure is commonly measured. The optical plethysmography measurement may then be divided by the blood pressure measurement to calculate a resulting index, which the inventor have coined the optical plethysmography index. In a healthy patient, a normal optical plethysmography index approximates one. Therefore, a decreasing optical plethysmography index, i.e. less than one, is indicative of perfusion failure or shock and/or the onset of perfusion failure or shock depending on when the measurement is taken.

Thus, laser-Doppler, ultrasound-Doppler, and other blood-flow measurement devices such as devices to measure surface perfusion pressure and optical plethysmography can be used to provide direct measures of blood flow in tissues. The present invention provides novel methods using such measurements to detect and quantify blood flow in tissues susceptible to low blood flow effective to detect perfusion failure in a patient. These measurements may be used in conjunction with each other and additionally in conjunction with measurements of pH, sublingual $PCO_2$, and $SaO_2$.

In order to assess perfusion failure in a patient, one first determines the expected range of blood-flow measurements for subjects of similar age and health status as the patient. Normal levels of blood flow may vary with the age of the subject. Health status may also be an important variable, since, for example, blood flow in a diabetic subject may differ from that of a subject not suffering from diabetes. Next, the blood flow in a mucosal tissue of the patient is determined. The blood-flow value is compared with the expected value for a normal subject determined in the first step; patient blood-flow values that are significantly lower than the normal values indicate perfusion failure. In addition, the rate-of-change of the patient's blood flow is measured over time with the blood-flow sensor. Rising values of blood flow indicate recovery, while declining values of blood flow indicate a worsening of the patient's condition.

The correlation of perfusion failure with decreased blood flow in several bodily tissues, including sublingual blood flow in particular, as well as the correlation of perfusion recovery and a corresponding increase in sublingual blood flow as blood volume recovers, was tested in an animal model that simulates a sudden loss or shedding of blood, such as might be caused by a gunshot wound or other severe wound. Perfusion recovery was simulated by subsequently reperfusing the animals with a blood infusion. Blood flow in the several tissues was assessed by counting (at autopsy) the numbers of colored microspheres deposited in various tissues under the indicated conditions, as described in Hale et al. (Circulation 78:428-434, 1988). The results are shown in FIG. 1. Blood flow in a tissue as a percentage of baseline (control) blood flow is plotted as a function of time during hemorrhage (induced blood-loss) and reinfusion of blood in an experimental animal. At the beginning of the test (BL), just prior to the time-point labeled "0," considerable blood was drawn from an animal that was previously in good health, the blood being drawn within a period of a few minutes. Aortic pressure drops rapidly during the first few minutes of such a test. In a subsequent period of about two hours, the aortic pressure remained about 40-50% below normal. The graph shows that tongue and sublingual blood flow decreased to about 35% during the first hour, showing a more dramatic response than other tissues. These data show that an decrease in sublingual blood flow is directly correlated with the effects of blood loss, i.e. perfusion failure.

The relationship of sublingual blood flow and recovery of blood volume (i.e., during perfusion recovery) was tested by infusing the animal with a blood infusion at 120 minutes. Aortic pressure rapidly increases during this period; similarly, sublingual blood flow rapidly recovered.

In addition to blood flow, as described above, $PCO_2$ or pH may also be measured in the animal or patient, at the same time or shortly before or shortly after such blood-flow measurements are made, to provide further information useful for assessing perfusion failure in an animal or a patient. $PCO_2$ and pH may be measured using any suitable technique, as will be appreciated by those skilled in the art.

For example, $PCO_2$ may be measured using a $CO_2$ sensor such as a pH-sensing $PCO_2$ sensor. Such $PCO_2$ sensors may have, for example, a membrane that is permeable to $CO_2$, and that separates a sodium bicarbonate or carbonic acid ($HCO_3$) solution from the environment. A pH sensor in the device measures the pH of the sodium bicarbonate solution. Two exemplary $CO_2$ sensors of this type are manufactured by Microelectrode, Inc. and Nihon Kohden (ISFET $PCO_2$ sensor).

Alternatively, the $CO_2$ sensor is an optical $PCO_2$ sensor. Structures, properties, functions, and operational details of fiber optic chemical sensors can be found in U.S. Pat. Nos. 4,577,109; 4,785,814; and 4,842,783, as well as in Seitz, "Chemical Sensors Based on Fiber Optics," Anal. Chem. 56(1):16A-34A (1984). Fiber optic sensors for monitoring $CO_2$ that may be suitable for use in the present invention include, but are not limited to, those described in U.S. Pat. Nos. 4,800,886; 4,892,383; 4,919,891, 5,006,314; 5,098,659; 5,280,548; and 5,330,718. Other exemplary fiber optic $CO_2$ sensors are described in Peterson et al. "Fiber Optic Sensors for Biomedical Applications," Science 224 (4645):123-127 (1984) and Vurek et al. "A Fiber Optic $PCO_2$ Sensor," Annals Biomed. Engineer. 11:499-510 (1983).

A suitable optical $CO_2$ sensor is described in U.S. Pat. No. 5,714,121 ('121) to Alderete et al., which pertains to an optical $CO_2$ sensor and method of manufacture thereof; a preferred sensor system and method of using the aforementioned optical $CO_2$ sensor is described in U.S. Pat. No. 5,672,515 ('515) to Furlong. In general, the sensor of the '121 patent is composed of a single optical fiber having a distal tip and a proximal region for communication with a means for receiving a signal from the distal tip. Light of a predetermined wavelength is directed through the optical fiber towards the distal tip, and emitted fluorescent light returns along the fiber to be detected and converted to a $CO_2$ concentration value. A capsule, composed of a $CO_2$-permeable silicone material, is arranged over the distal tip at a predetermined position. The capsule contains an indicator solution having a suitable pH-sensitive indicator component, generally a fluorescent dye, and substantially no air. Examples of fluorescent dyes include without limitation fluorescein, carboxyfluorescein, seminaphthorhodafluor, seminaphthofluorescein, naphthofluorescein, 8-hydroxypyrene 1,3,6-trisulfonic acid, trisodium salt ("HPTS") and dichlorofluorescein, with HPTS particularly preferred. A sealing means provides a liquid-tight seal and affixes the capsule onto the distal tip.

Optical $CO_2$ sensors are generally used by contacting the distal end of the sensor with a mucosal surface as described herein. Light of a predetermined wavelength is directed from an external source, through the optical fiber, impinging distally on the encapsulated indicator composition. The intensity of the emitted fluorescent light returning along the fiber is directly related to the concentration of $CO_2$ in the sample, as a result of the pH-sensitive indicator material present at the fiber tip (i.e., the pH of the indicator solution is directly related to $CO_2$ concentration, as a result of carbonic acid formation). The emitted light is carried by the optical fiber to a device where it is detected and converted electronically to a $CO_2$ concentration value. The sensor may additionally have a reference dye present in the indicator composition. The intensity of the light emitted from the reference dye may be used to compensate, via ratioing, the signal obtained from the indicator. A more preferred system for determining $PCO_2$ is described in the '515 patent, directed to a simultaneous dual excitation/single emission fluorescent sensing method, wherein light of two different wavelengths is used to excite a single fluorescent indicator species, with one of the two wavelengths at the isosbestic point. The two fluorescence emission signals that result are ratioed to provide the desired measurement.

Suitable pH sensors include optical pH sensors as described in U.S. Pat. Nos. 5,536,783 and 5,607,644 to Olstein et al. Such optical sensors include a chemical pH sensor means, capable of responding to changes in pH in nearby tissues and fluids, that is incorporated into a fiber optic waveguide assembly so as to interact with the environment into which the pH sensor means is placed. The sensor may be placed in a patient's body, and more particularly, may be placed adjacent a mucosal surface in a patient's body. Typically, the responses of the chemical sensor cause changes in the optical properties of the chemical sensor/optical waveguide assembly, so that pH changes near the tip of the assembly may be monitored and assessed by the user at another portion of the apparatus, e.g., at a portion of the apparatus remaining external to the patient's body. For example, as described in the aforementioned U.S. patents, the pH sensor means may comprise a fluorescent poly(urethrane) copolymer that fluoresces in response to irradiation, wherein the fluorescence is dependent on the pH of the environment being monitored.

The results of experiments in the animal model, as shown in FIG. 1, can be extrapolated to represent a human subject suffering perfusion failure, such as that associated with a gunshot wound or a severe cut from machinery or a knife. Thus, a patient will suffer a rapid decrease in aortic pressure during blood loss, until the outflow of blood is stopped by application of pressure or other means to stop bleeding. The present invention takes advantage of the relationship between blood flow (in the GI tract or the upper respiratory/digestive tract, including in such tissues as sublingual, tongue, stomach and so forth) and perfusion failure or perfusion level, to provide methods and devices to assist a physician or other health care provider in the diagnosis and treatment of a patient having or susceptible to a condition associated with perfusion failure.

For example, although assistance from a paramedic or other person may be available shortly after the initial primary insult, it may take thirty minutes or more for the patient to reach a hospital. This lapse in time may make it difficult to accurately assess the condition of the patient and the presence and/or severity of perfusion failure. Measuring and/or monitoring sublingual blood flow according to the present invention allows the physician or other healthcare provider to readily detect the level of blood flow relative to normal, as well as the rate of change of blood flow. A rapid decrease in blood flow suggests that the patient has suffered a loss of blood within the last hour or so, while low blood flow indicates the patient presently suffers from a low level of aortic pressure and perfusion failure. In this manner the invention can be used to assess the patient's condition, allowing for appropriate and rapid selection of an appropriate therapy.

The present invention can also be used to monitor the efficacy of reperfusion or other therapeutic regimen to treat perfusion failure in the patient. For example, if the physician, paramedic, or other emergency provider determines that a transfusion of blood or blood components is indicated, and the transfusion is successful in rapidly increasing aortic pressure (such as that illustrated in FIG. 1 from 120 minutes onward), then this success will be reflected by a rapid recovery in blood flow (as illustrated in FIG. 1 from 120 minutes onward). FIG. 1 shows that sublingual blood flow measurements provide a good indication of the level of perfusion failure.

Figure 2:
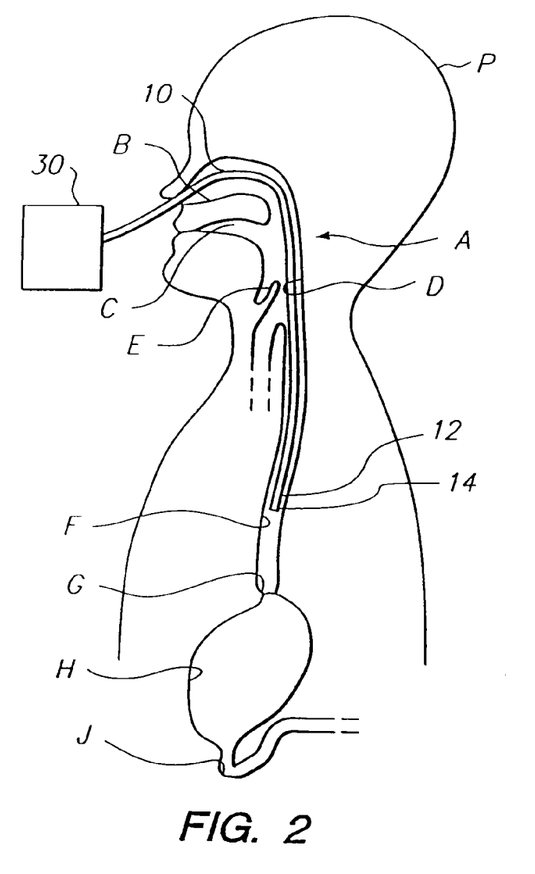
FIG. 2 is a partial sectional view showing a sensor of the present invention in place in one of many acceptable positions within the GI tract of a patient.

In the present invention, the inventors disclose that a useful measurement of perfusion failure can be obtained by measuring blood flow anywhere in the GI tract or the upper respiratory/digestive tract. Although FIG. 2 illustrates the upper portion of the GI tract, it is to be understood that the invention may be practiced by placement of a blood-flow sensor adjacent any mucosal surface accessible by the outh or nose and connecting with the GI tract or upper respiratory/digestive tract. Accordingly, by way of illustration, FIG. 2 shows the upper respiratory/digestive system or tract A of a person, and particularly including the nasal passage B, the oral cavity C, and the upper portion D of the throat that extends to the top of the epiglottis E. The upper respiratory/digestive tract includes, without limitation, the esophagus F, and the gastrointestinal tract includes, without limitation, the esophagus F, the esophageal sphincter G, the stomach H, and the intestines J. Insertion of a catheter 10 with a blood-flow sensor 12, through the nose or mouth B, C, past the epiglottis E, and into the esophagus F so that the end 14 of the catheter with the sensor 12 thereat lies adjacent a mucosal surface within the esophagus.

Preferably, the sensor may be positioned in the upper respiratory/digestive tract A, preferably with the sensor lying above, at the surface of, or at the epiglottis E so it does not have to pass by it. More preferably, the sensor is placed at a site within the oral-nasal cavity, e.g., within the nasal cavity, the mouth (e.g., under the tongue at a site in contact with the tongue or the floor of the mouth, between a region of the lip and gum or the cheek and gum, the roof of the mouth, or the soft palate), or at a site within the pharynx. Most preferably, the sensor is placed adjacent a mucosal surface at a site that will avoid the patient's gag reflex or otherwise minimize discomfort.

The blood-flow sensor lies adjacent a mucosal surface in the upper respiratory/digestive tract A, in order that it effectively measures blood flow in the tissue. Placement of a blood-flow sensor adjacent a mucosal surface of the upper respiratory/digestive tract A according to the present invention provides a very good quantification of perfusion failure at all times, including the most critical minutes after the onset of perfusion failure when treatment is likely to be most effective.

Figure 3:
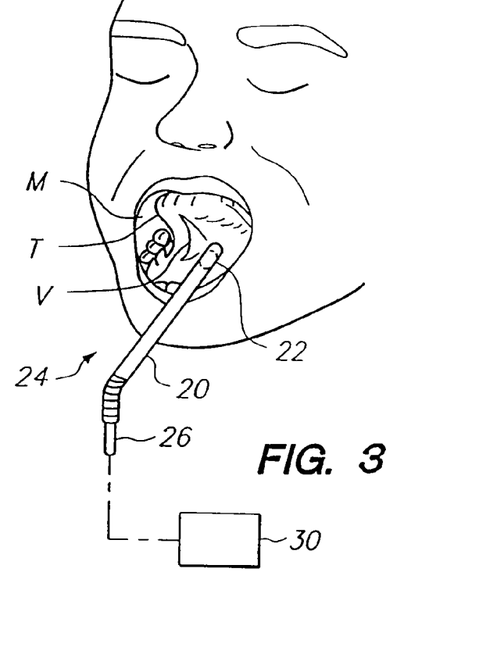
FIG. 3 is an isometric view showing a sensor of the present invention as it is introduced into the mouth of a patient, for sublingual placement.

FIG. 3 shows one embodiment of a device or apparatus of the present invention, wherein a tube 20 containing a blood-flow sensor 22 at its front end, is inserted into the oral cavity and placed under the tongue T of the patient, preferably to one side of the frenulum V. After insertion, it might be desirable if the mouth M of the patient is kept closed around the tube. However, as with other instruments commonly inserted through the mouth, and as with a patient in a critical condition, the patient is usually unable to keep his mouth closed. In such cases the device can be adapted with a holder as described below.

Figures 4, 6:
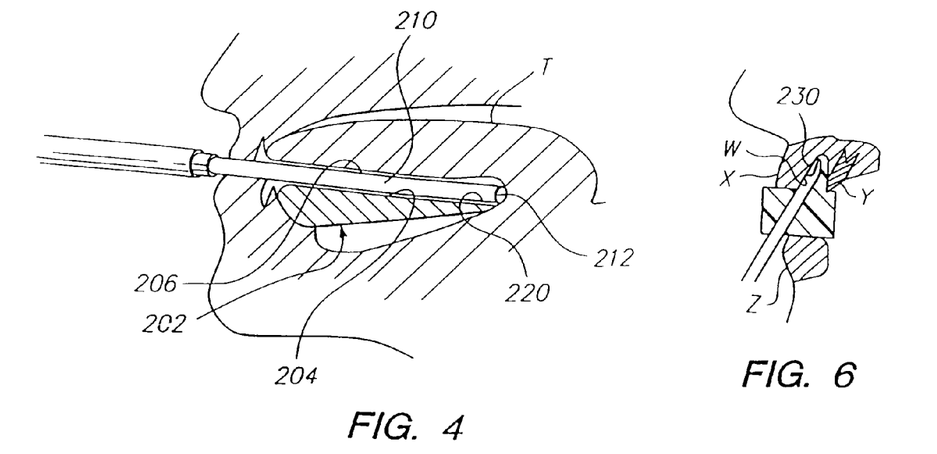
FIG. 4 is a sectional view of a sensor assembly and holder constructed in accordance with an embodiment of the invention, shown lying in a patient's mouth.
FIG. 6 is a sectional view of a sensor assembly and holder of another embodiment of the invention, shown holding a sensor between a lip and teeth of a patient.

As illustrated in FIG. 3, the tube 20 and sensor 22 are part of an instrument 24 that includes a flexible cable 26 that extends to a test instrument 30 that typically indicates the blood flow which provides an indicia of a degree of perfusion failure. While the tube 20 is substantially rigid, the cable 26 is flexible. The cable 26 can be made highly flexible for ease of use, instead of having only the moderate flexibility of a catheter. Usually catheters require enough flexibility to pass through curved body passages, but yet must be resistant to column-type collapse in order to withstand the force applied to the catheter's proximal end necessary to accomplish insertion of the distal end and movement of the distal end along the body passage. Since the cable 26 in the device of FIG. 3 does not have to be pushed, it can have more flexibility for ease of use. The largely rigid tube 20 preferably has a length of no more than about one foot (one-third meter), since a longer length would be cumbersome. Catheters for insertion through the esophagus into the stomach, generally have a length of much more than two feet. FIG. 4 shows an example of a sensor 212, which lies against the sublingual mucosal surface.

Figure 5:
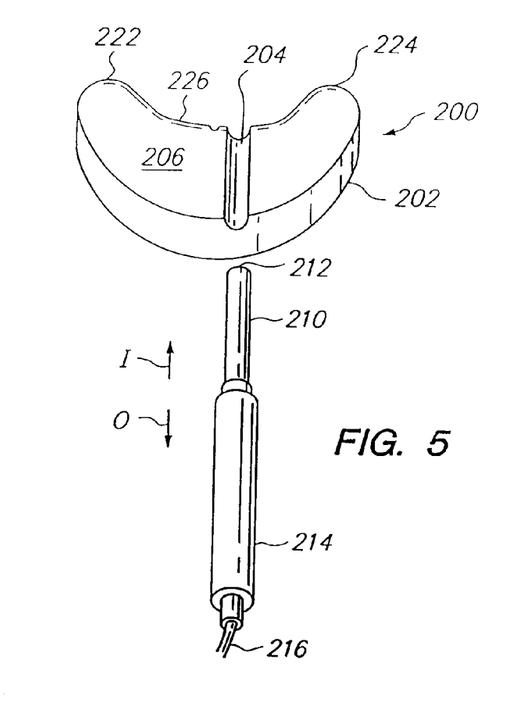
FIG. 5 is an isometric view of the holder of FIG. 4.

FIG. 5 shows a preferred embodiment of the device of the invention that is suitable for taking sublingual blood flow measurements. In this embodiment, sensor assembly instrument 214 may be held in position by a sensor holder 202 that is shaped to lie primarily in a patient's mouth. The holder 202 forms a holder passage 204 that extends between the inner and outer portions 202, 226 of the holder. When located in place, the sensor 214 projects inwardly from the holder and substantially directly contacts the mucosal surface of the patient. The frame may have an outer end that lies outside the patient's mouth.

The holder 202 can serve to prevent discomfort to the patient. To this end, the sublingual inner portion 226, including portions 222 and 224, of the holder preferably lies close to the walls of the mouth on opposite sides of the sensor 214, as well as above and below the sensor. The upper surface 206 of the holder is designed so the tongue T can lie on at least its inner portion, to further provide a seal and to support the tongue to avoid tiring the patient. The holder 202 can also serve as an aid to prevent drying of the oral-nasal cavity.

While the holder is an exemplary and preferred isolating means for use with the present invention, other isolating means that serve substantially the same function can be substituted or used in conjunction with the holder. For example, a sheath can surround the blood-flow sensor. The sensor and the sheath can be held in place by a holder similar to that described above, but with the advantage that the entire device may be of an overall smaller size (e.g., for placement in the mouth).

A second purpose of the holder is to substantially fix the position of the sensor assembly 214 and the sensor 212 so the sensor is maintained in a proper position and does not move. This is particularly useful where the patient is incapable of holding the sensor properly in place due to unconsciousness or some other reason. A tension coil spring extending between the handle and holder, can be used to gently urge the sensor 212 inwardly, where necessary. The holder 202 is preferably formed of an elastomeric material (Young's modulus of less than 50,000 psi) such as a soft rubber or soft foam, to avoid high localized pressure on the patient's mouth that could cause discomfort. In one embodiment, the sensor is positioned on either side of the frenulum of the tongue. The rear portion of the holder 226 may be shaped, as with a slot or bevel, to comfortably receive the frenulum, so the sublingual inner portion can lie close to the inner end of the sublingual area and therefore closely around the blood-flow sensor.

Figure 7:
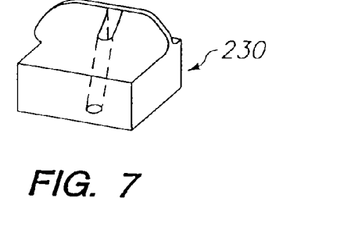
FIG. 7 is a front isometric view of the holder of FIG. 6.

In an alternative embodiment, the sensor can be placed adjacent any mucosal surface accessible by the mouth or nose and connecting with any region of the GI tract or upper respiratory/digestive tract. For example, in FIG. 6 the sensor 230 can be placed at a gingival mucosal surface W that lies between a lip X and the teeth Y of the patient. The area at the rear of the upper or lower lips X, Z is a mucosal surface. FIGS. 6 and 7 illustrate a holder 230 suitable for use at a mucosal surface adjacent a patient's lips. In this embodiment, holder 230 is preferably of soft elastomeric material such as an elastomeric solid or a foam, or even a viscous fluid in a flexible shell. The holder isolates the mucosal surface area contacted by the sensor and prevents movement of the sensor.

Figure 8:
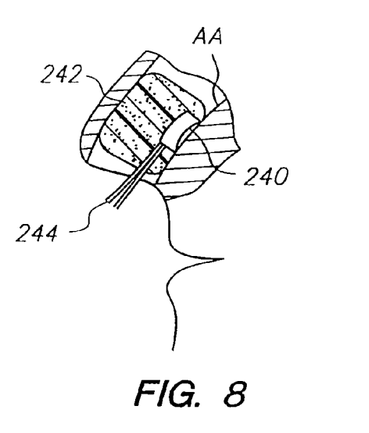
FIG. 8 is a sectional view of a sensor assembly and holder of another embodiment of the invention, shown holding a sensor in the nose of a patient.

In another embodiment, the blood-flow sensor 240 lies adjacent a mucosal surface area AA in the vestibule of the nasal cavity of a patient (FIG. 8). A foam plug 242 serves as a holder that holds the sensor to position it. Only a pair of electrical wires 244 extend from the sensor through the holder. Where the blood-flow sensor is a fiber optical sensor, the holder can be adapted accordingly so that only the optical fiber extends from the plug.

In another embodiment, the blood-flow sensor may be placed adjacent any mucosal surface in the nasal cavity of a patient.

In another embodiment, the blood-flow sensor may be placed adjacent any mucosal surface in the middle nasal conchae of a patient.

In another embodiment, the blood-flow sensor may be placed adjacent any mucosal surface in the inferior nasal conchae of a patient.

In another embodiment, the blood-flow sensor may be placed adjacent any mucosal surface in the choana of a patient.

In another embodiment, the blood-flow sensor may be placed adjacent any mucosal surface in the pharyngeal opening of the auditory tube of a patient.

In another embodiment, the blood-flow sensor may be placed adjacent any mucosal surface in the pharynx of a patient.

In another embodiment, the blood-flow sensor may be placed adjacent any mucosal surface in the oropharyngeal passage of a patient.

In another embodiment, the blood-flow sensor may be placed adjacent a mucosal surface in the stomach of a patient.

In another embodiment, the blood-flow sensor may be placed adjacent a mucosal surface in the jejunum of a patient.

In another embodiment, the blood-flow sensor may be placed adjacent a mucosal surface in the colon of a patient.

In another embodiment, the blood-flow sensor may be placed adjacent a mucosal surface in the rectum of a patient.

In another embodiment, a $PCO_2$ sensor may be used in conjunction with the blood-flow sensor. Alternatively, a pH sensor may be used in conjunction with the blood-flow sensor. In a further embodiment, both a pH sensor and a $PCO_2$ sensor may be used in conjunction with the blood-flow sensor. The advantages of such a combination in providing a more robust indication of perfusion failure will be well understood by those skilled in the art.

The blood-flow sensor used in the methods and devices of the invention may be any blood-flow sensor suitable for detection of blood flow in the manner described herein, such as laser-Doppler blood-flow sensors, ultrasound-Doppler blood-flow sensors, imaging sensors and so forth. For example, the preferred blood-flow sensor is a laser-Doppler blood-flow sensor.

An exemplary blood-flow sensor of this type is manufactured by Vasomedics (2963 Yorkton Blvd., St. Paul, Minn. 55117-1064; (800) 695-2737)). For example, the Laserflo $BPM^2$ may be used to provide continuous tissue perfusion data which can be used to practice the present invention.

In an alternative embodiment of the present invention, the blood flow measurement taken with the blood-flow sensor placed against a mucosal surface may be used in conjunction with the SPP index and/or the optical plethysmography Index. In order to assess perfusion failure in a patient with this alternative embodiment, one first determine the expected range of measurements for subjects of similar age and health status as the patient as normal measurements of surface perfusion pressure and optical plethysmography may vary with the age of the subject. For a healthy patient, these two indices will be close to one. The blood flow in a mucosal tissue of the patient is determined. Next, the surface perfusion pressure and/or the optical plethysmography measurement is taken. Each of these values are compared with the expected value for a normal subject; patient values that are significantly lower than the normal values indicate perfusion failure. In addition, the rate-of-change of the patient's blood flow is measured over time with these three measurements. Rising values of blood flow, and an SPP index and an optical plethysmography index close to one indicate recovery, while declining values of blood flow and an SPP index and an optical plethysmography index less than one indicate a worsening of the patient's condition.

As there are many co-morbid factors, e.g. diabetes, that may affect an accurate measurement of blood flow, the use of blood flow measurements, in particular sublingual blood flow, in conjunction with the SPP index and the optical plethysmography index allows the physician to more accurately monitor perfusion failure and recovery. These measurements may also be used in conjunction with each other and additionally in conjunction with measurements of pH, sublingual $PCO_2$, and $SaO_2$.

Figure 9:
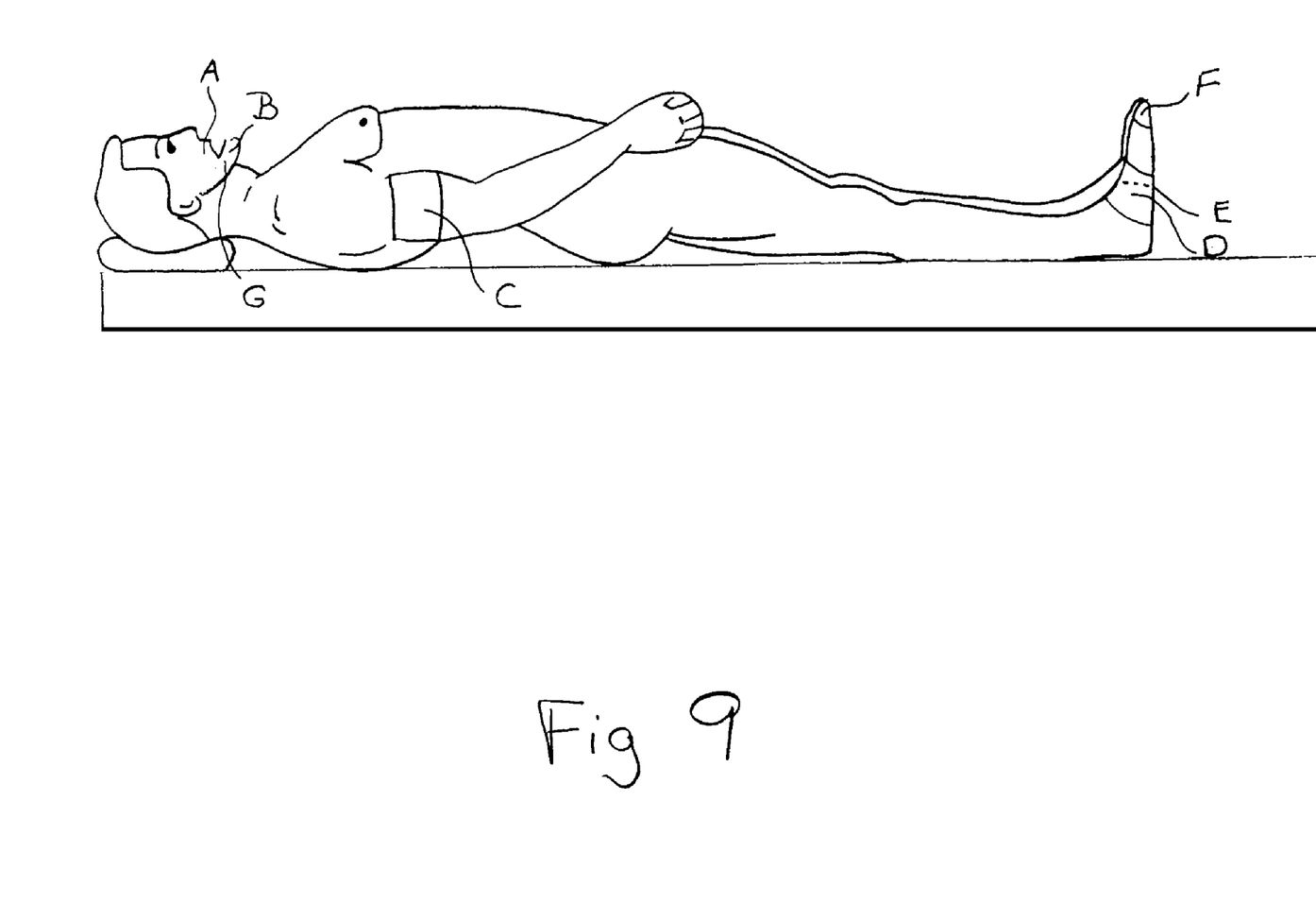
FIG. 9 is an illustration of a patient and the points at which various measurements in accordance with the present invention may be taken.

Referring to FIG. 9, an illustration of a patient and the points at which various measurements in accordance with the present invention are taken are depicted. At referenced point A measurements of sublingual $CO_2$ and/or pH may be taken. At reference point B blood flow may be measured with the blood flow sensor in accordance with the present invention. At reference point G, $SaO_2$ may be taken. Blood pressure may be taken at reference point C (brachial pressure) or at point F (toe pressure), or at other common reference points on the body such as thigh and non-invasive arterial pressure. The illustrated patient is shown in the prone position. If a measurement of brachial pressure is used, the patient may be sitting or standing. However, if other reference points are used, the patient should by lying prone so that the measurement of pressure in on the same level as the heart. A sensor depicted at E is placed under cuff D to measure surface perfusion pressure.

Thus, the invention provides a method and device for assessing perfusion failure, which methods may be performed rapidly, with little equipment set-up required, and with minimal or substantially no invasion, and thus minimal risk of harm to the patient and an improved probability of patient compliance. The method generally involves introducing a blood-flow sensor adjacent any mucosal surface accessible by the mouth or nose and connecting with the GI tract of a patient, or the upper respiratory/digestive tract of a patient, taking a measurement of surface perfusion pressure and brachial pressure, for example, to calculate the SPP index, taking a measurement of optical plethysmography and brachial pressure, for example, to calculate the optical plethysmography index and assessing perfusion failure by comparing these measurements with normal values. The invention is useful in a variety of settings, such as in triage in emergency and disaster settings, monitoring in anesthesia, intensive care, and other acute settings in which patients may have acute perfusion failure (shock).

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains. All patents, patent applications, journal articles and other references mentioned herein are incorporated by reference in their entireties.

What is claimed is:

1. A device for assessing the degree of systemic perfusion in a patient, the device comprising:
   a. a surface perfusion pressure monitor for measuring the surface perfusion pressure of a patient; and
   b. a blood pressure monitor for measuring the blood pressure of the patient;
   wherein the device derives an index from the surface perfusion pressure measurement and the blood pressure measurement to assess the degree of systemic perfusion of the patient.

2. The device of claim 1, wherein the surface perfusion pressure monitor includes a laser Doppler sensor.

3. The device of claim 2 wherein the index derived is a surface perfusion pressure index.

4. The device of claim 1 wherein the surface perfusion pressure monitor includes a photoplethysmograph.

5. The device of claim 4 wherein the index derived is an optical plethysmography index.

6. The device of claim 1 further comprising a blood flow sensor adapted to be positioned adjacent a mucosal surface within a patient's body for taking a measurement, directly or indirectly, the measurement selected from the group consisting of sublingual $PCO_2$, and $SaO_2$.

7. The device of claim 6 further comprising a sensor for measuring pH.

8. A method for assessing the degree of systemic perfusion in a patient comprising the steps of (i) measuring the surface perfusion pressure in the patient by utilizing a surface perfusion pressure monitor; (ii) measuring blood pressure in the patient; (iii) calculating an index with a processor derived from the surface perfusion pressure measurement and the blood pressure measurement; and (iv) assessing the degree of systemic perfusion of the patient.

9. The method of claim 8 wherein the step of measuring the surface perfusion pressure in a patient includes taking the measurement with a laser Doppler sensor.

10. The method of claim 9 wherein the step of calculating an index derived from the surface perfusion pressure measurement and the blood pressure measurement includes calculating a surface perfusion pressure index.

11. The method of claim 8 wherein the step of measuring the surface perfusion pressure in a patient includes taking the measurement with a photoplethysmograph.

12. The method of claim 11 wherein the step of calculating an index derived from the surface perfusion pressure measurement and the blood pressure measurement includes calculating an optical plethysmography index.

13. The method of claim 8 further comprising the step of (v) taking a blood flow measurement adjacent a mucosal surface accessible by a mouth within a patient's body selected from the group consisting of sublingual $PCO_2$ and $SaO_2$.

14. The method of claim 13 further comprising the step of (vi) providing a pH sensor for measuring pH.

* * * * *